United States Patent [19]

Spangler

[11] Patent Number: 5,083,019

[45] Date of Patent: Jan. 21, 1992

[54] PRECONCENTRATOR FOR ION MOBILITY SPECTROMETER

[75] Inventor: Glenn E. Spangler, Lutherville, Md.

[73] Assignee: Environmental Technologies Group, Inc., Baltimore, Md.

[21] Appl. No.: 571,172

[22] Filed: Aug. 21, 1990

[51] Int. Cl.$^5$ .................. B01D 59/44; H01J 49/00
[52] U.S. Cl. ...................... 250/286; 250/282; 250/287
[58] Field of Search ............... 250/282, 286, 287, 288, 250/423 R

[56] References Cited

U.S. PATENT DOCUMENTS

| | | | |
|---|---|---|---|
| 3,621,239 | 11/1971 | Cohen | 250/41.9 |
| 3,621,240 | 11/1971 | Cohen | 250/41.9 |
| 4,259,573 | 3/1981 | Prober et al. | 250/287 |
| 4,311,669 | 1/1981 | Spangler | 422/98 |
| 4,390,784 | 6/1983 | Browning et al. | 250/287 |
| 4,551,624 | 11/1985 | Spangler et al. | 250/287 |
| 4,712,008 | 12/1987 | Vora et al. | 250/287 |
| 4,732,046 | 3/1988 | Lawrence et al. | 73/864.21 |
| 4,839,143 | 6/1989 | Vora et al. | 422/98 |
| 4,987,767 | 1/1991 | Corrigan et al. | 73/864 |

Primary Examiner—Bruce C. Anderson
Attorney, Agent, or Firm—Leonard Bloom

[57] ABSTRACT

A system for and a method of increasing the sensitivity of organic vapor detection in ion mobility spectrometer by as much as three (3) orders of magnitude. Vapors are collected from the gas to be analyzed by controlled adsorption and are subsequently thermally released as an enriched concentration into the reactor volume of an ion mobility spectrometer. The herein disclosed system of preconcentrator and ion mobility spectrometer is easier to maintain and is more portable than other instruments of comparable sensitivity and the reliable operation is simpler. In one experiment, the computed enrichment factor of 3,500 for the preconcentrator lowered the limit of detection from 10 ppt for the ion mobility spectrometor alone down to 0.003 ppt for the embodiment of this invention. The sensitivity, compactness, ease of operation and ruggedness make the invention a suitable choice as a sensitive, efficient, and rapid detector of narcotics, toxic and explosive materials. Such detectors find applications at airports, surface transportation terminals, facility inspection points and security stations.

30 Claims, 11 Drawing Sheets

PRECONCENTRATOR FOR ION MOBILITY SPECTROMETER

BACKGROUND OF THE INVENTION

1. Field Of The Invention

This invention relates to an ion mobility spectrometer, and more particularly, to an ion mobility spectrometer having increased sensitivity and especially useful for the detection of involatile compounds such as drugs, explosives and controlled substances.

2. Description Of The Prior Art

This invention relates to ion mobility spectrometry otherwise known as plasma chromatography. The operation of the ion mobility spectrometer is similar to the operation of a time-of- flight mass spectrometer, the difference being that the time-of-flight spectrometer operates in a vacuum (where the mean free path of the contained gases is many times the dimension of the gas container) whereas the ion mobility spectrometer operates at or near atmospheric pressure (where the mean free path of the contained gas is smaller than the dimensions of the container).

The purpose and utility of an ion mobility spectrometer is the identification of one or more gas or vapor constituents in a sample gas and the measurement of the respective concentrations. The sensitivity or limit of detection determines the power of the spectrometer, and much of the prior art is dedicated to various aspects of ion mobility spectrometer sensitivity. Specialized improvements in sensitivity and specificity have been made, but a significant increase in sensitivity is needed to sample involatile (vapor pressures $\leq 10^{-6}$ mm Hg) vapors.

A typical ion mobility spectrometer, such as that disclosed by Cohen et al in U.S. Pat. No. 3,621,240 issued Nov. 16, 1971, comprises a reaction chamber and, an ionization source associated with the reaction chamber. The reaction region is conventionally defined as the volume enclosed by the ionization source. The ionization source generates reactant ions which react with a sample contained within the reaction region, thereby forming product ions. The typical ion mobility spectrometer also includes ion drift chamber, an ion injector shutter or grid interposed between the ion reaction chamber and the drift chamber, and an ion collector.

U.S. Pat. No. 4,259,573 which was issued on Mar. 31, 1981 to J. M. Prober et al., describes one improvement for determining small concentrations of chemical compounds by plasma chromatography. Small known increments of species A plus (optionally, another calibrant species) are introduced in turn into a plasma chromatograph together with the unknown sample chemical, and the respective changes in the amplitude or area of the characteristic ion peak of species A in the unknown sample are measured.

U.S. Pat. No. 4,311,669, which was issued on Jan. 19, 1982 to G.E. Spangler and assigned to the assignee herein, described an improvement wherein a sample inlet port of an ion mobility detector has a membrane interface. The sample which is included as a vapor component in a gas stream impinges on the exterior surface of the membrane and penetrates the membrane and is carried into the ion mobility spectrometer by a carrier gas which scrubs the interior surface of the membrane. The membrane serves as both a selection device and barrier which operates to increase the sensitivity and specificity.

U.S. Pat. No. 4,551,624, which was issued on Nov. 5, 1985 to G.E. Spangler et al. and assigned to the assignee herein, describes a different improvement wherein a reagent such as acetone and/or carbon tectrachloride is injected into the carrier gas prior to entering the reaction region. The reagent has a higher proton affinity, electron affinity or acidity than contaminants in the sample gas; a lower proton affinity, electron affinity or acidity than at least one constituent of the sample gas to be detected; and does not cluster with water disposed in the reagent source.

U.S. Pat. No. 4,839,143, issued on June 13, 1989 to K.N. Vora et al. and assigned to the assignee herein, describes a selective ionization source for an ion mobility spectrometer in which an electrolytic reaction with an alkali salt heated to a predetermined temperature reacts with the atoms and molecules in the carrier gas to produce ions with mobilities characteristic of the atoms and molecules. The invention disclosed in this '143 patent is a non-radioactive ionization source and further provides a means for ionization of a broad class of compounds.

In another improvement of ion mobility spectrometers, as described in U.S. Letters Pat. No. 4,732,046 issued on Mar. 22, 1988 to A. H. Lawrence et al., samples are condensed on a sample tube in the form of a hypodermic needle. This sample tube is subsequently heated and the sample is desorbed into a carrier gas which delivers the sample to the ion mobility spectrometer. Some enrichment of the sample concentration may result.

The above cited improvements in the sensitivity of ion mobility spectrometers are important in particular applications. Nevertheless, the improvements fall short of the sensitivity required to detect involatile vapors from say explosives, drugs, pharmaceuticals, and the like; and it would be desirable to provide an ion mobility spectrometer having substantially improved (5 to 6 orders of magnitude) sensitivity.

SUMMARY OF THE INVENTION

Accordingly, it is an object of the present invention to provide an ion mobility spectrometer having a preconcentrator device which increases the sensitivity of the ion mobility spectrometer and thus provides a resultant concentration enrichment by a factor as large as 1000, thereby providing a system having sensitivity and prompt response for the detection of involatile compounds.

A preconcentrator is a device which collects sample vapors typically on a cool or active surface for adsorption when exposed to the sample and releases the adsorbed vapor, generally at enriched concentrations, into the gas phase when the cool or active surface is heated. When a preconcentrator is the input to a detector (as taught by the present invention) sample vapors are first adsorbed on the cool or active surface by causing ambient air with the sample to flow across the surface by means of a sample pump. Second, the active surface is transported and inserted into the reactor volume of the ion mobility spectrometer. Third, the adsorbed vapors are released by heating. At the same time, the active element is electrically biased to a voltage such that ions formed in the reactor volume are guided away from the active element and probe towards the drift region of the ion mobility spectrometer. An enhancement of sensitivity results. By using an efficient adsorbing surface, minor constituents of the input gas are totally, if adsorption is ideal, trapped on the surface. By inserting the active surface into the reactor volume, the desorbed vapors are efficiently exposed to ionization radiation without loss due to inefficient transport through inlet plumbing.

In accordance with the teachings of the present invention, there is herein illustrated and described, an apparatus for increasing the sensitivity of vapor concentration measurements in ion mobility spectrometers. The apparatus includes an active surface element on which selected vapors and gases are collected during an adsorption cycle. This active surface element is mounted on a probe, and the probe carries the active surface element during an adsorption cycle in the gas to be analyzed and subsequently positions the active surface element in the reactor volume of the ion mobility spectrometer during a desorption cycle. Means of heating the active surface element are provided to thermally desorb the collected vapors and gases, and means of electrically biasing the element at a positive or negative voltage (depending on ion polarity) are provided to inhibit the collection of ions on the element and drive the ions toward the drift region, thereby producing an enriched input concentration to the ion mobility spectrometer. Means are further provided for cooling the degassed active surface element before its return to the initial sampling position. Additional means are provided for the repetitive transport of the probe and the active surface element between the sampling position in the gas to be analyzed and the degassing position in the reactor volume of the ion mobility spectrometer.

In accordance with the further teachings of the present invention, there is herein disclosed, an improved method for increasing the sensitivity of vapor concentration measurement in ion mobility spectrometers. This improved method includes the step of, first, collecting an amount of the vapor by adsorption on an active surface exposed to the gas to be analyzed. Next, the active surface is transported and inserted into the reactor volume of an ion mobility spectrometer; and the active surface is heated, thereby thermally desorbing the adsorbed vapors. The released vapors are entrained in the small carrier gas stream in the ion mobility spectrometer. The active surface is electrically biased to guide ions in the reactor volume towards the drift region. The vapor concentration in the ion mobility spectrometer is much higher than the original concentration in the gas to be analyzed, and the limit of detectability is lowered by a factor equal to the enrichment ratio. Thereafter, the active surface is cooled and returned to the sampling position.

In a preferred embodiment, the present invention provides a transport means for the repetition of the method steps with optimum sampling and analysis times.

By choosing metal wires or coated metal wires as the preconcentrator active surface in a preferred embodiment of the invention, the active surface element can be rapidly heated and rapidly cooled.

The present invention further provides for a plurality of probes, each carrying an active surface element, whereby one probe is in the sampling position while another is in the analysis position in the ion mobility spectrometer. By means of a plurality of probes, sampling times can be shortened by simultaneously performing the adsorption and desorption steps and maximizing the efficiency with which the ion mobility spectrometer is used for sample analysis. This is allowed because the ion mobility spectrometer clears rapidly of sample desorbed in its reactor volume and desorption times are much less than adsorption times. Shortened sampling times and high achievable sensitivity make the present invention suitable for real time detection of low level vapor concentrations from involatile compounds such as explosives, drugs, pharmaceuticals, and the like.

In addition to the detection of explosives and of drugs, the sensitivity, cost effectiveness, speed, simplicity of operation and maintenance make the system of the present invention an attractive choice for monitoring toxic gases and vapors, organometallic and inorganic compounds, salts and very fine particles for which the preconcentrator is coupled with an aerosol collector, mobility analyzer or particle impactor.

Coatings may be applied to the active surface area in accord with the teachings of this invention in order to increase the active surface area, to adjust heats of adsorption, solubility, or all the above. Different wire materials may be used, and the active surface may be charcoal or molecular sieve.

In another aspect of the present invention, the adsorbing area and the probe upon which it is mounted are an integral part of a sliding shuttle which rapidly and repetitively carries the active surface element from the sampling position in the gas to be analyzed to the analysis position in the reaction volume of the ion mobility spectrometer.

These and other objects of the present invention will become apparent from a reading of the following specification, taken in conjunction with the enclosed drawings.

BRIEF DESCRIPTIONS OF THE DRAWINGS

DETAILED DESCRIPTION OF THE PREFERRED EMBODIMENTS

Figure 1:
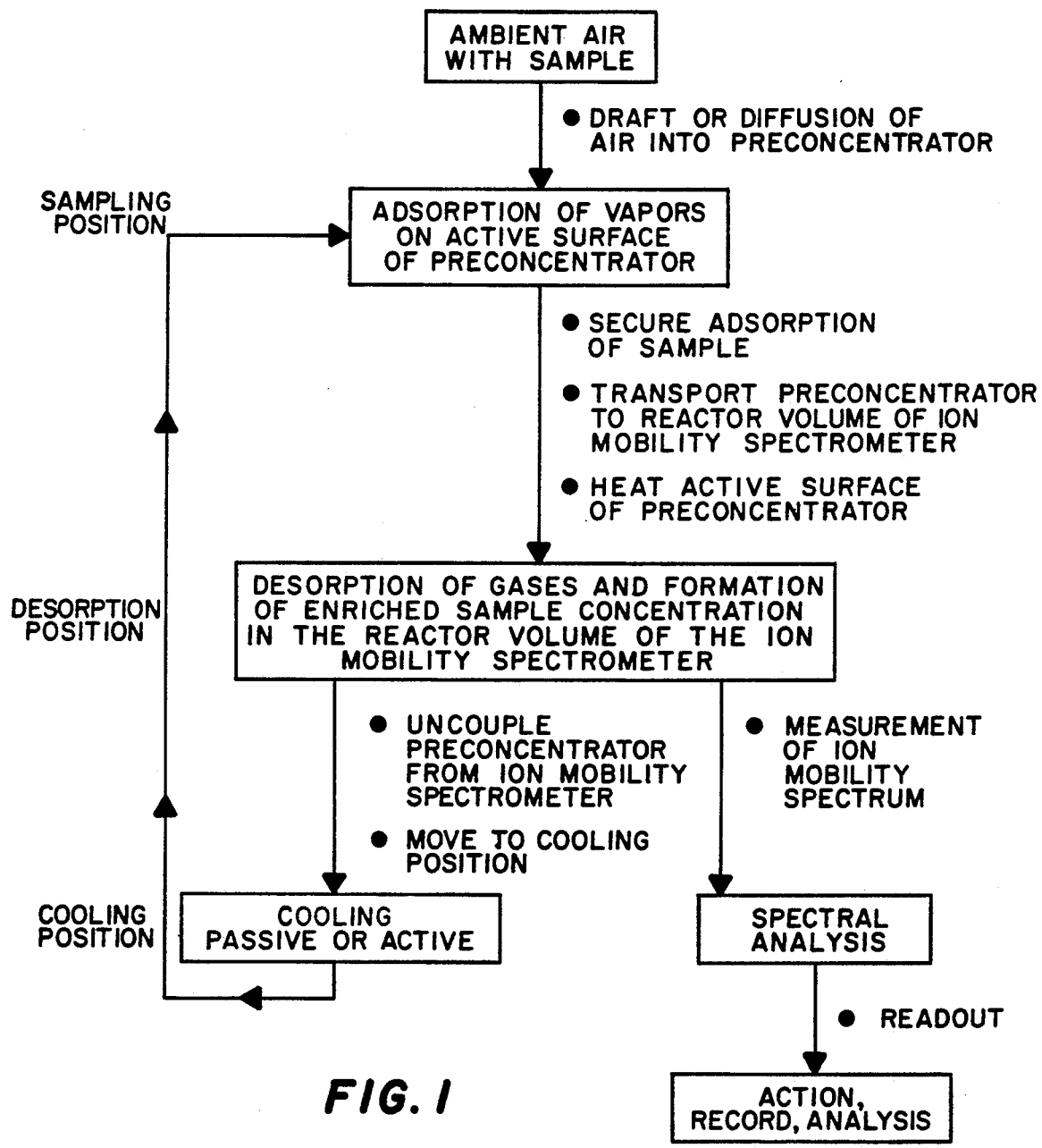
FIG. 1 is a chart showing the complete sequence of steps in the improved method of the present invention.

Referring to FIG. 1, the embodiments of the invention complete the cycles as shown. Ambient air with the sample is allowed to come into contact with the active area element of the preconcentrator which collects atoms and molecules by adsorption. This can be done by simply exposing the active area of the probe to the air containing the sample or drawing air containing the sample across the active surface. To minimize dilution of sample, simple exposure is preferred. After a predetermined period of time in the sampling position, adsorption is stopped and the preconcentrator is transported to the desorption or analysis position at the ion mobility spectrometer. The active area element is inserted into the reactor volume, and heat is applied to desorb the collected vapors into the carrier gas of the ion mobility spectrometer. The desorbed gases are ionized immediately in the reactor volume, and in order to preclude spurious trapping of the ionized sample on the active surface or on the probe, the active surface area is electrically biased to guide the ions toward the drift region.

Desorbed gases produce an enriched concentration of the vapors for analysis, and the enrichment factor is the factor by which the sensitivity of the ion mobility spectrometer is improved. The enrichment factor, E, defined as the ratio of the enriched concentration to the initial concentration, can be determined empirically or calculated using the theoretical equation which represents the present invention:

$$E = \frac{\gamma P A_c t_c}{Q_c t_r \sqrt{2\pi m k T}} \times \frac{22,400}{6.023 \times 10^{23}}$$

$A_c$ = area of active element for adsorption
$t_c$ = adsorption time
$Q_c$ = carrier gas flow rate
$t_r$ = desorption time
m = molecular mass
k = Boltzmann's constant
T = temperature Under the conditions of one experiment, the estimated enrichment factor was 3500 which when superimposed on the 10 ppt limit of detection for an ion mobility spectrometer corresponds to a limit of detection of approximately 0.003 ppt for the system.

Once degassed, the preconcentrator is uncoupled from the ion mobility spectrometer and moved to a position where the active adsorbing area is cooled by either passive or active means. The cool preconcentrator is transported back to the sampling position where it is again exposed to the gas to be analyzed. The cycle is repeated.

Figure 2:
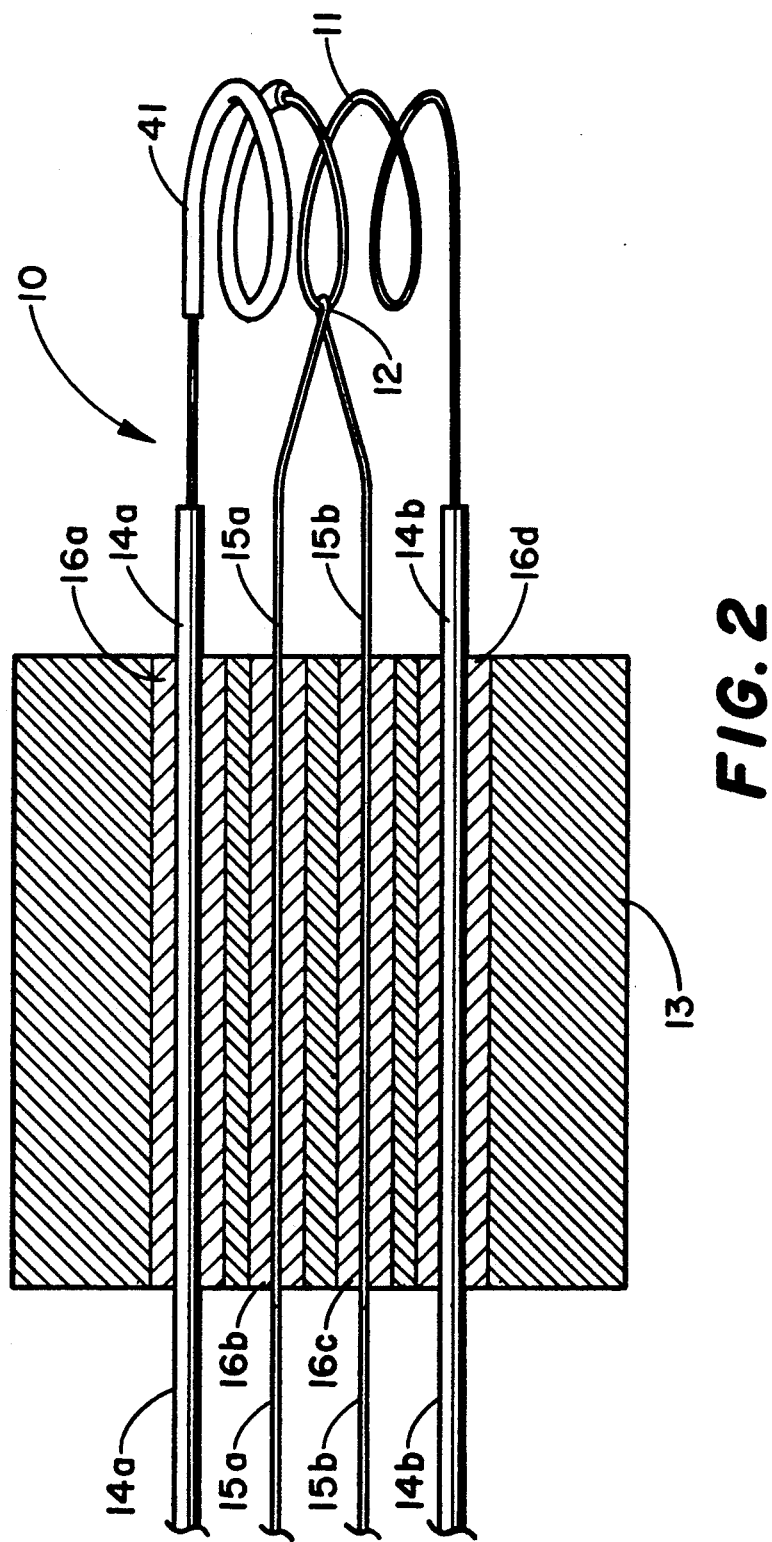
FIG. 2 show a helical wire adsorbing/desorbing element mounted on a cylindrical probe body.

Referring to FIG. 2, the active area element 11 of the preconcentrator 10 is mounted on the probe body 13 which is shown in cross section. The wire 11 of the active area may be coated, as at 41, and is connected to leads 14a and 14b which are insulated from the probe body 13 by insulating sleeves 16a and 16d. The temperature of the active area coil is measured by thermocouple 12 the electrical signals from which are carried by leads 15a and 15b which are insulated by sleeves 16b and 16c. For probe bodies made as one ceramic unit, the insulating sleeves are not necessary; and the conductors may be metallization strips.

Figure 3:
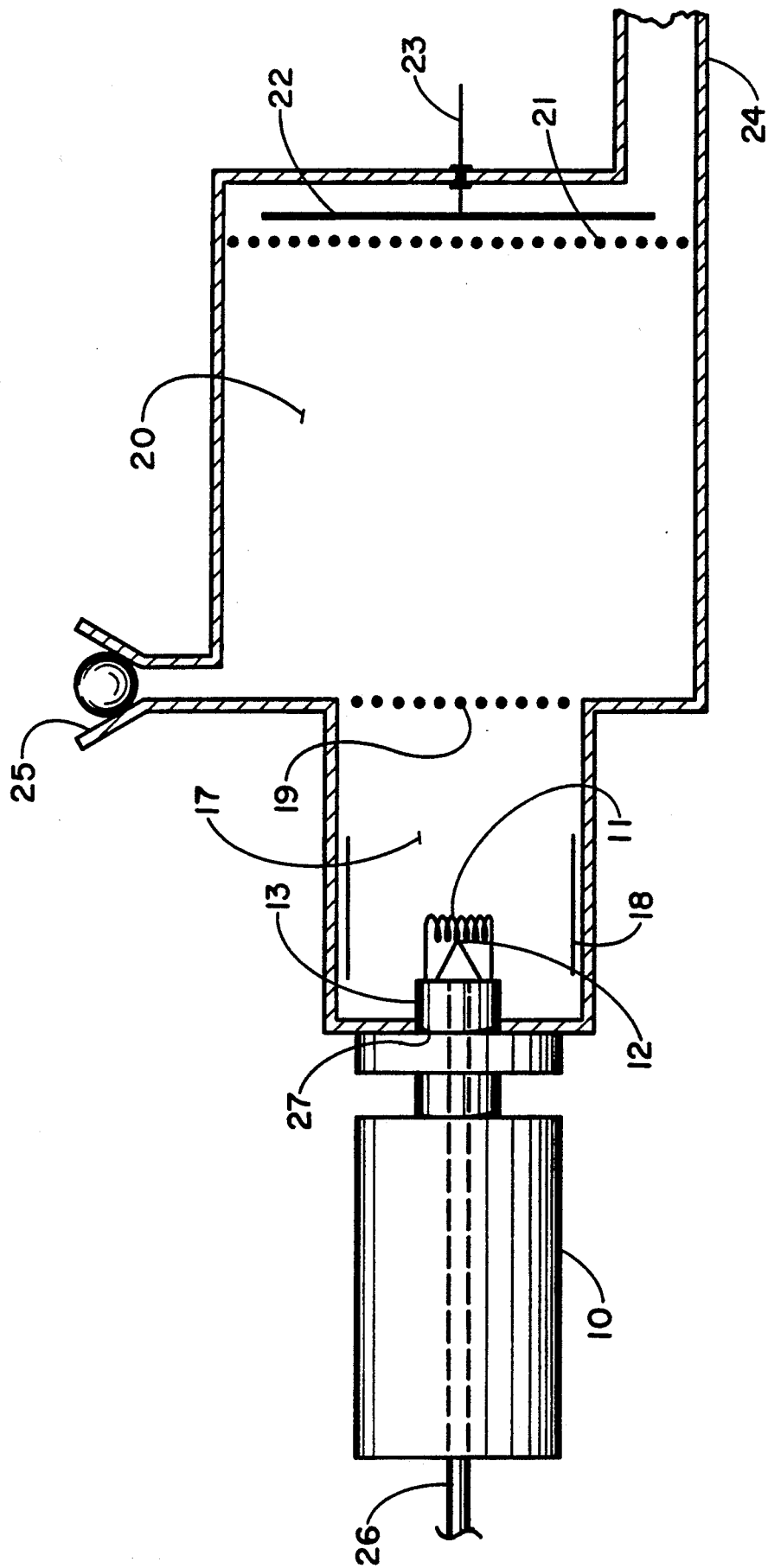
FIG. 3 is the schematic diagram of a preconcentrator coupled with an ion mobility spectrometer.

FIG. 3 shows the wire helix active area 11 with thermocouple 12 inserted into the reaction volume 17 of the ion mobility spectrometer (IMS). The probe 13 protrudes through electrically insulated aperture 27 to position the active area in the reaction volume 17. Ionization is provided by electrons from the $^{63}$Ni radioactive source (foil) 18. During the desorbing cycle the active area 11 is heated by passing a current through the wire coil, and the temperature is monitored with thermocouple 12. At the same time, the active element is electrically biased to a voltage which precludes collection of sample ions by the active area of the probe. Provision is made for a carrier gas flow through inlet 26 which carries and mixes the desorbed gases in the reactor volume 17 where ionization takes place primarily through ion/molecule reactions with reactant ions. The shutter grid 19 injects a group of ions of all kinds into the drift region 20 where an electric field drives the ions toward the aperture grid 21 and the signal collector plate 22. Ions of different specie arrive at the collector plate 22 at different times depending upon the respective mobilities. A drift gas is provided through inlet 24 and exhausted along with the carrier gas through outlet 25 which may have a ball check valve or some other restriction.

Figure 4:
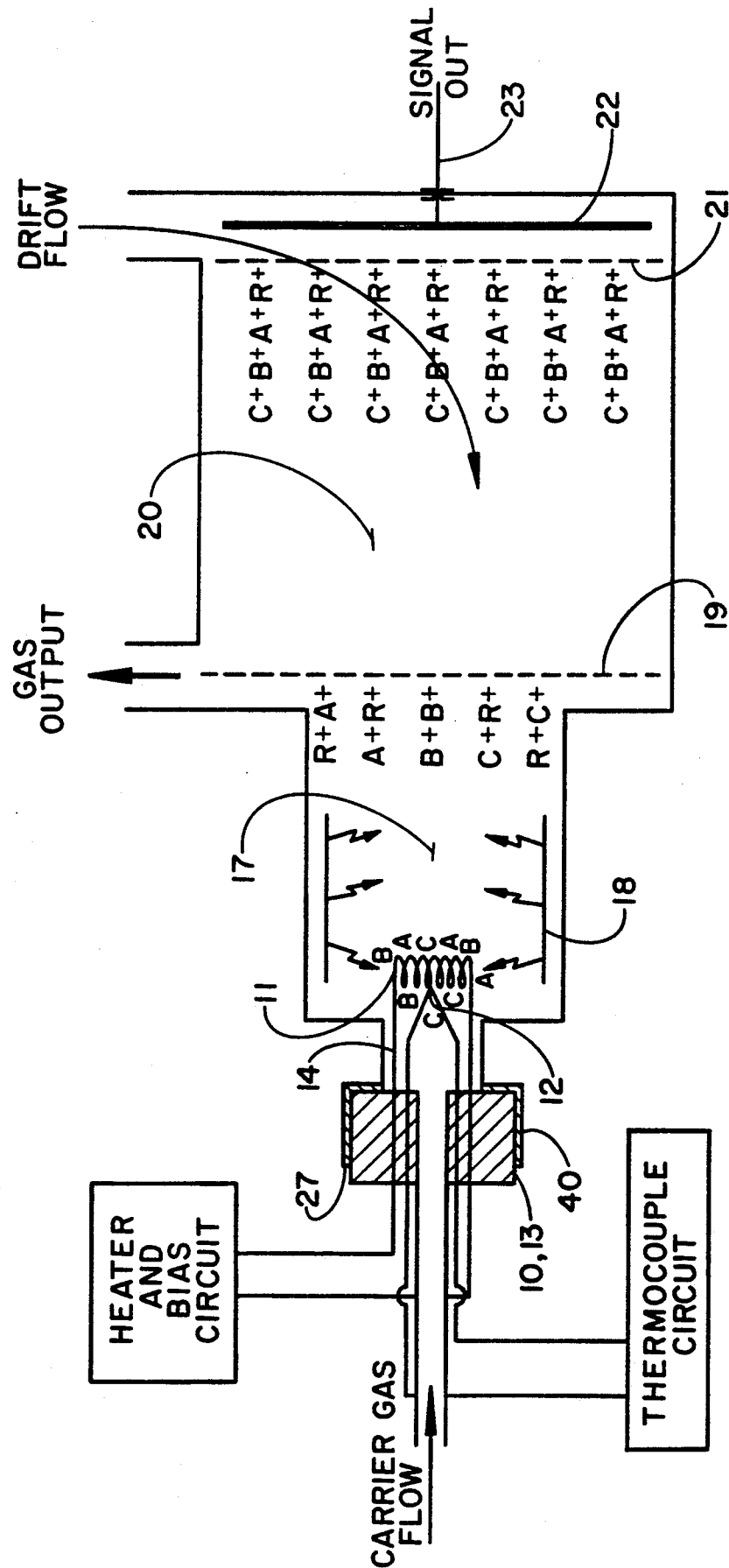
FIG. 4 is a schematic diagram of a preconcentrator inserted into an ion mobility spectrometer and a spatial distribution of ions, showing a circuit for heating and biasing the active area, and further showing an additional circuit for thermocouple measurements.

FIG. 4 is a schematic diagram of an embodiment which shows the preconcentrator probe 13 with the wire active area 11 inserted into the reaction volume 17 of the ion mobility spectrometer. The probe is seated on insulator 40 in the aperture 27. Schematically shown are the adsorbed vapor molecules A, B, C being carried on the surface of the wire adsorber 11. The wire element is heated by passing the current through it and the adsorbed molecules A, B, C, are entrained in the carrier gas in the reaction volume. The molecules are ionized to form ions A+, B+ and C+ by the ionizing beta $\beta^-$ rays emitted by the $^{63}$Ni radioactive source. The dominant process for producing sample ions is through ion/molecule reactions of sample molecules with ionized carrier gas molecules. The ion flux which migrates towards the shutter grid 19 under the action the bias voltage on the active area and probe includes ions of the samples in question A+, B+, C+ and an abundance of reactant ions R+. The shutter grid 19 releases a group of ions at a time marking the beginning of the drift across the drift region 20 under the action of an electric field. The spectral resolution of an ion mobility spectrometer arises out of the differences in mobilities (or travel times) of different ions. Here shown is a schematic of spatial separation of ions arriving at the collector plate in order of decreasing mobility (increasing travel time): R+, A+, B+ and C+.

Figure 5:
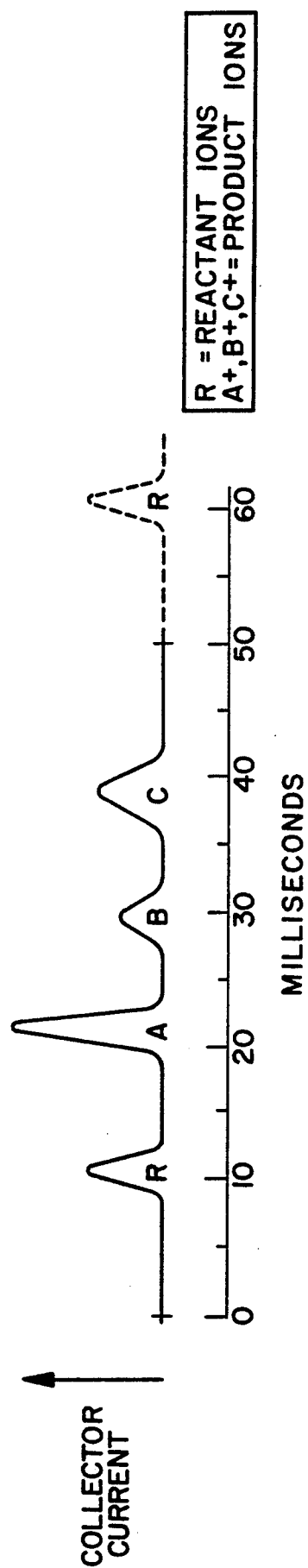
FIG. 5 shows a drift time spectrum for ions with the same sequence of decreasing mobilities as in FIG. 4.

FIG. 5 shows a drift time spectrum in which collector current is plotted against drift time. This separation of groups by mobility is shown in the time domain whereas the separation shown in FIG. 4 was in the spatial domain. The sequence of decreasing mobilities is the same in FIG. 4 and FIG. 5.

Figure 6:
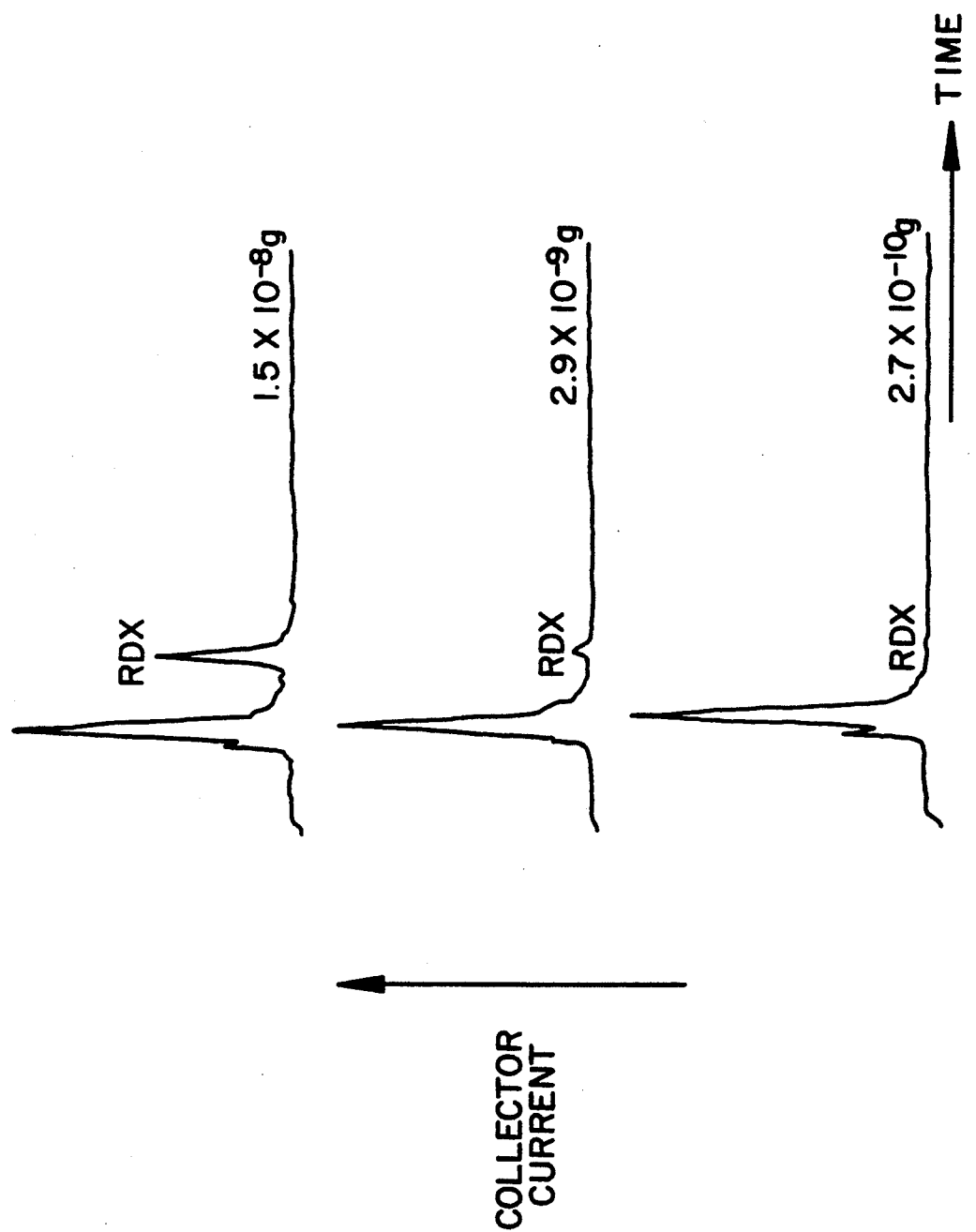
FIG. 6 shows the response of an ion mobility spectrometer with a preconcentrator to various amounts of RDX.

FIG. 6 shows the response of an ion mobility spectrometer with a preconcentrator to various quantities of RDX. These data were collected by depositing known quantities of RDX on the active wire element using a syringe. Nanogram quantities of RDX were easily detected. Additional studies showed that a typical sensitivity for an ion mobility spectrometer is 10 ppt and an achievable enrichment factor for the preconcentrator probe is approximately 1000. Thus, the resultant overall sensitivity of ions with a preconcentrator probe is on the order of 0.01 ppt.

Figure 7:
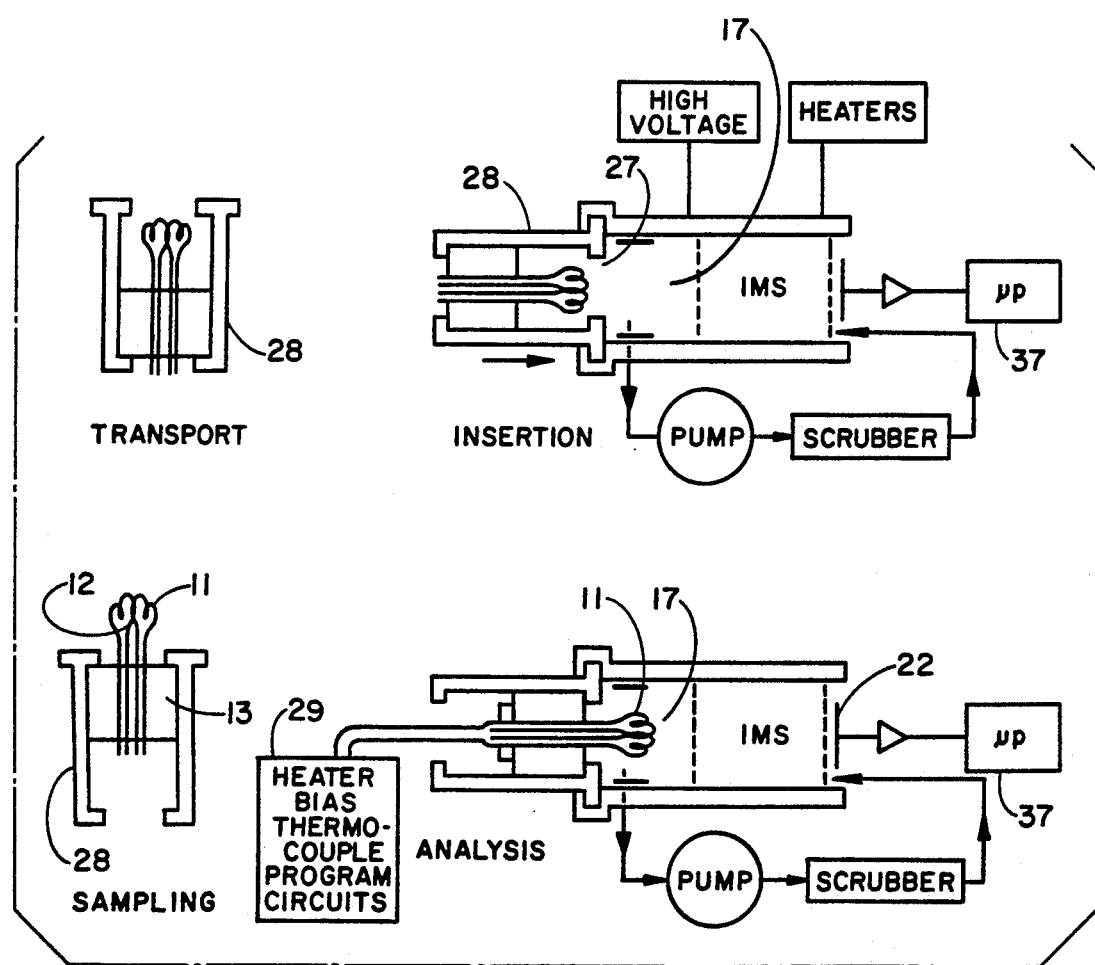
FIG. 7 is a schematic showing a complete cycle of sampling and analysis using a preconcentrator.

FIG. 7 is a schematic diagram for the complete sequence of preconcentrator positions in a possible implementation for the preconcentrator probe. Sampling wire 11 is exposed to the gas to be analyzed in the sampling position. The adsorber element 11 is withdrawn into a housing 28 during transport from the sampling station to the analysis station. The transport housing 28 is seated in the electrically insulated aperture 27 at one end of the reactor volume 17 during the insertion stage. The probe block 13 positions the wire active element 11 in the reactor volume 17 during the analysis period. Power for heating the wire element to degas the adsorbed vapors and power for the voltage bias of the active area 11 and the probe 13 are provided by circuits 29 which also control the heating and cooling cycle, and monitor the temperature by means of thermocouple 12. The signal from collector 22 is amplified and transmitted to a microprocessor 37 for spectral analysis and display. After the sampling element 11 is degassed and cooled, the probe block 13 is withdrawn into the transport case 28 which is then disconnected from the ion mobility spectrometer and carried to the sampling station where the cycle is repeated.

Figure 8:
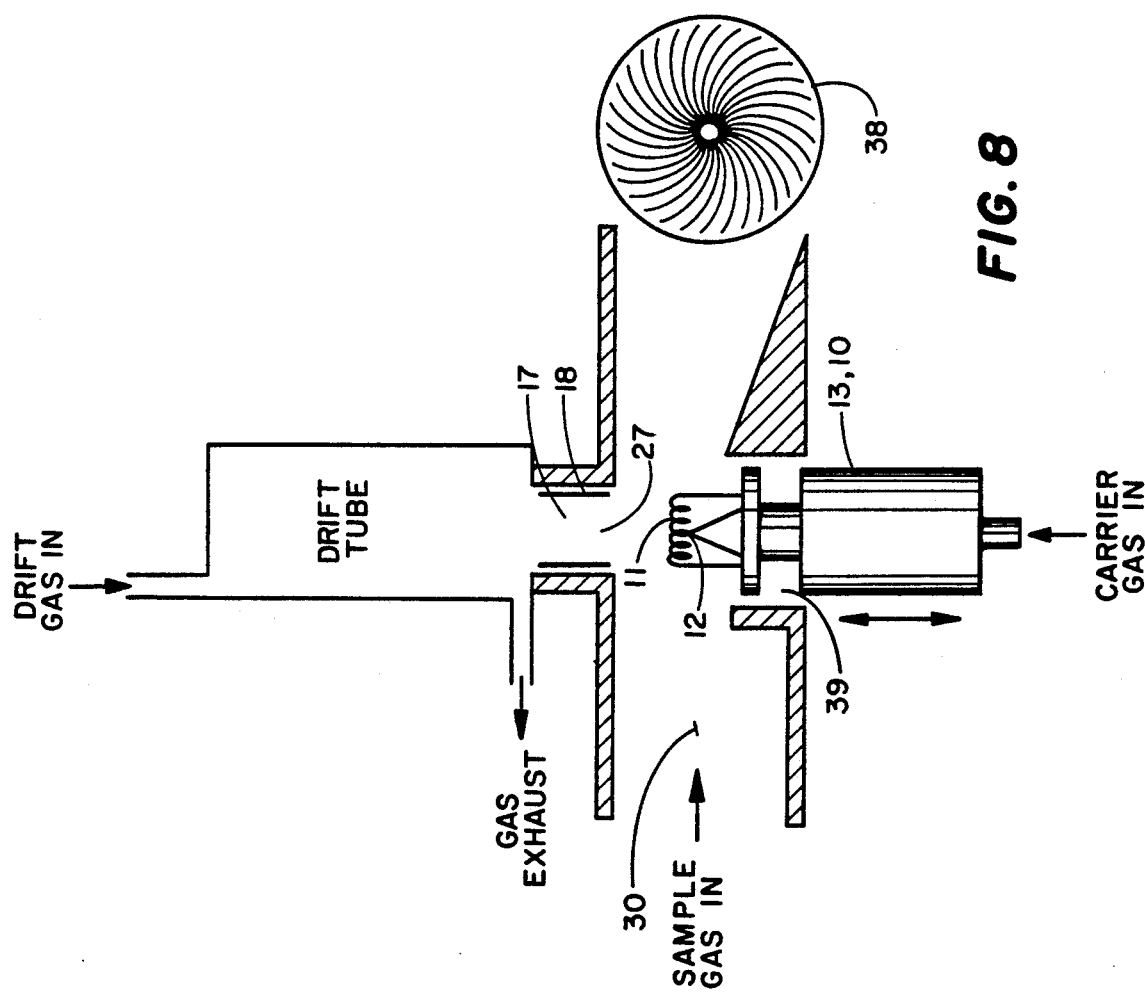
FIG. 8 is a schematic showing a shuttle carrying the probe and the wire active area between the sampling and analysis positions.

FIG. 8 is another approach to using the preconcentrator probe. Here a shuttle is used to transport the probe and wire coil back and forth between sampling and analysis positions. The probe body 13 is a part of the preconcentrator 10 which moves in a shaft 39 perpendicular to the sample gas duct 30 between a sampling position in which the wire filament 11 is exposed to the sample gas for sample adsorption and an analysis position in which the wire filament 11 is inserted into the reactor volume 17 through aperture 27. The filament 11 is heated by passing a current through it with the temperature monitored by thermocouple 12. Desorbed gases are ionized by the radioactive ionizer 18 in the presence of a carrier gas. The flux of ions is subsequently analyzed in the ion mobility spectrometer (IMS). The shuttle action minimizes the transport time between the sampling position and the analysis position.

Figure 9:
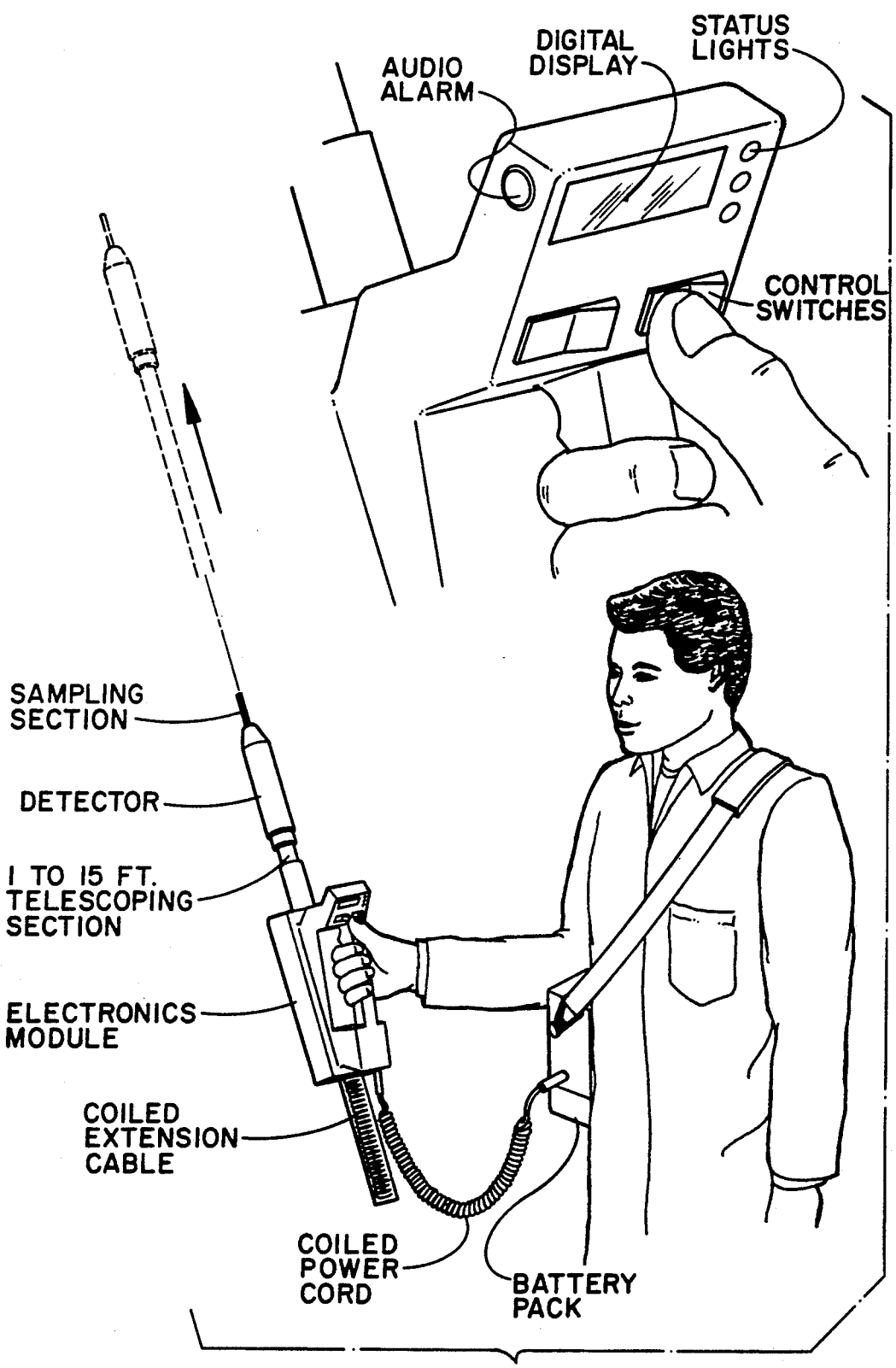
FIG. 9 illustrates an embodiment of the invention designed for the detection of narcotics.

FIG. 9 shows an embodiment in a detection system in which the fractional sampling time is doubled by mounting two probes in geometric opposition. When one probe is in the sampling position the other is in the analysis position. The probes exchange positions during the next half cycle. A cutaway drawing of this embodiment is shown in FIG. 10.

Figure 10:
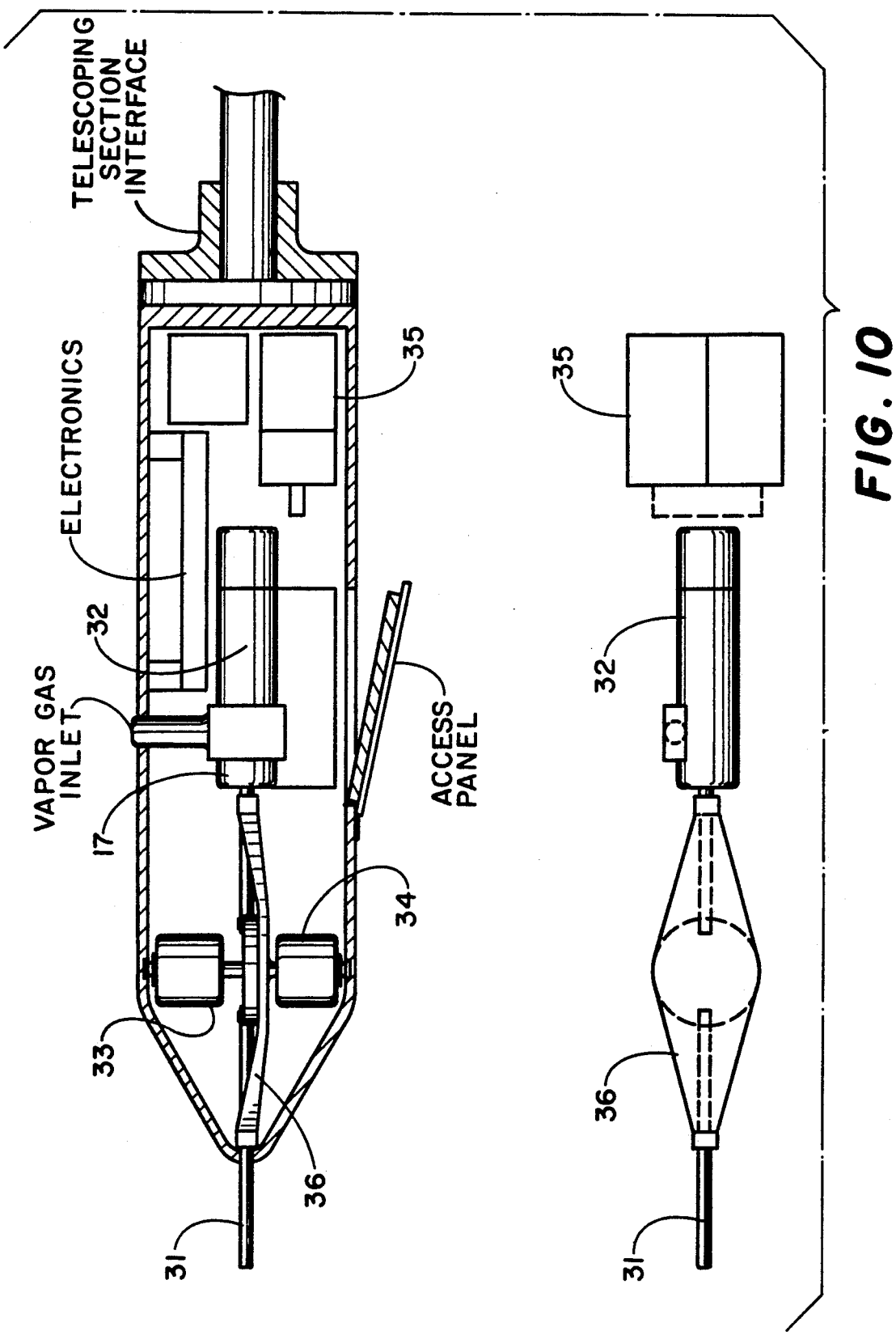
FIG. 10 shows a longitudinal section of the detector in FIG. 9.

FIG. 10 is a diagram of two-probe system. One of the hot wire probes 31 is in the sampling position while the other probe is inserted in the reactor volume 17 of the ion mobility spectrometer 32. To exchange positions, the probes are first withdrawn by the probe retractor 33 and then rotated on the rotation frame 36 by rotation motor 34. Also, shown in this figure is a vapor gas inlet to the ion mobility spectrometer for input through a selective membrane (U.S. Pat. No. 4,311,669).

Figure 11:
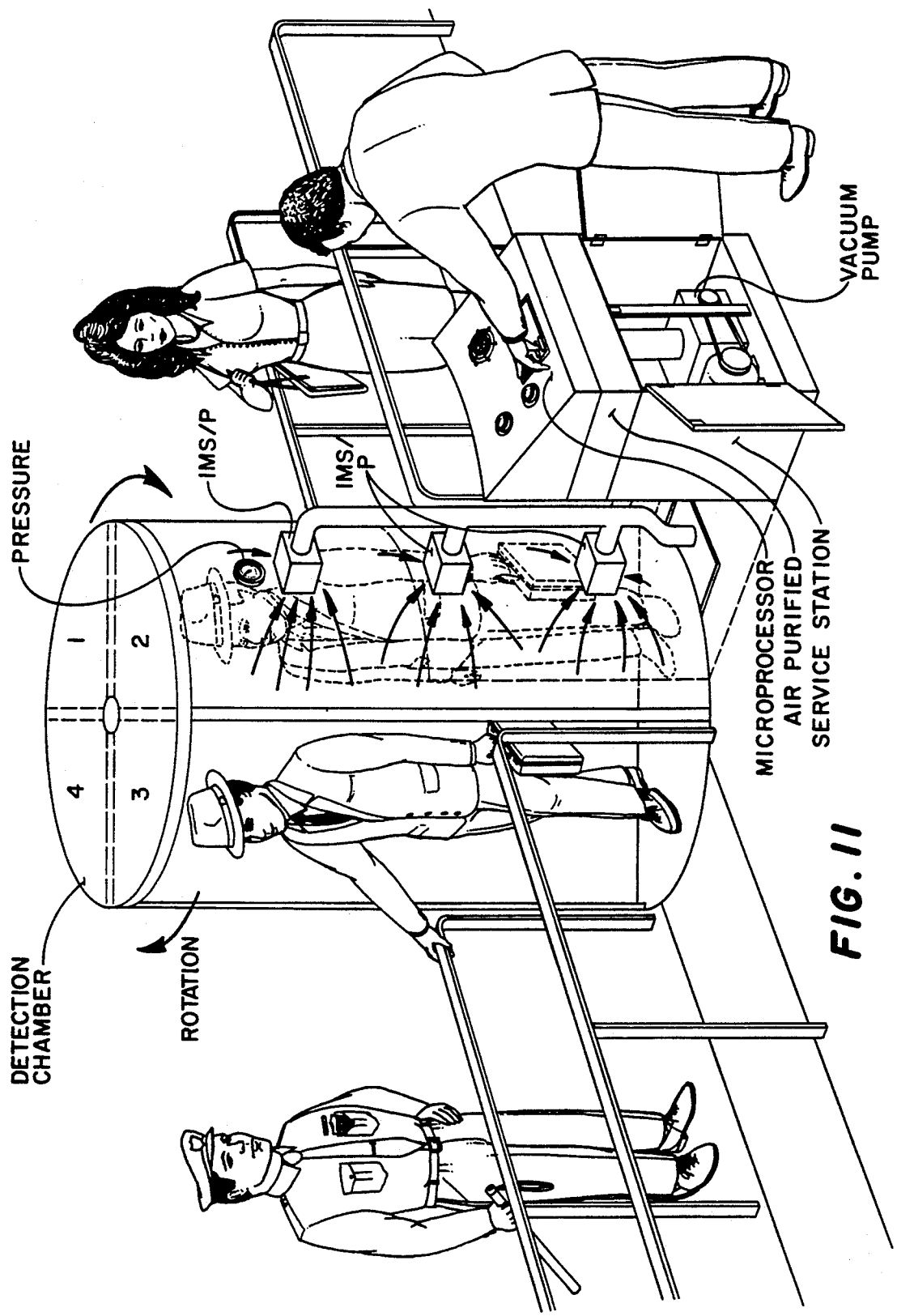
FIG. 11 illustrates an embodiment of the invention in a walk-through passenger screening system for explosive materials, narcotics and other controlled substances.

FIG. 11 illustrates an application of one of the preferred embodiments of the invention to a walk-through passenger screening system for detection of controlled substances such as narcotics and explosives. Three ion mobility spectrometers with preconcentrators (IMS/P) draw gas from the detection chamber. The short sampling time (less than ten seconds) and the concealment of the controlled substances means that the vapor concentrations are low. The present invention offers a unique combination of exceptional sensitivity, cost effectiveness, speed, simplicity of operation and ease of maintenance.

Obviously, many modifications may be made without departing from the basic spirit of the present invention. Accordingly, it will be appreciated by those skilled in the art that within the scope of the appended claims, the invention may be practiced other than has been specifically described herein.

The invention claimed is:

1. An apparatus for increasing the sensitivity of an ion mobility spectrometer to trace chemical vapors in a gaseous sample comprising a means for collecting said vapors from said gaseous sample, and a means for desorbing said vapors within a reaction region of said ion mobility spectrometer.

2. The apparatus of claim 1, wherein said collection means comprises an active surface element having a surface area on which said vapor is adsorbed, and said desorbing means comprises a source of electrical energy for heating said active surface element to thermally release said vapor.

3. The apparatus of claim 2, wherein the active surface element is coated for increasing said surface area, adjusting heats of adsorption of said vapors, solubility of said vapors, or all the above.

4. The apparatus according to claim 3, wherein said coating comprises one from among the following group of ceramic, gel, glass, zeolite and salt.

5. The apparatus according to claim 2, further comprising means for transporting said active surface element into and out of a port to the reaction region of said ion mobility spectrometer.

6. The apparatus of claim 5, wherein said transport means comprises a sliding shuttle for removing the active surface element from the reaction region of said ion mobility spectrometer during adsorption of said vapors, and for inserting the active surface element in said reaction region during desorption of said vapors.

7. The apparatus according to claim 6, wherein said sliding shuttle transports said active surface element automatically.

8. The apparatus according to claim 6, wherein said sliding shuttle is operated manually to transport said active surface element.

9. The apparatus according to claim 6, further comprising means for preventing entry of ambient air through said port during transportation of said active surface element by said sliding shuttle.

10. The apparatus according to claim 9, wherein said means for preventing entry of air further comprises a flow of purified gas out of said reaction region port.

11. The apparatus according to claim 2, wherein said active surface element is biased relative to a collector of said ion mobility spectrometer to cause ions formed in said reaction region to be repelled toward said collector, and wherein said source of electrical energy for heating said active surface element is electrically isolated from ground.

12. The apparatus according to claim 1, wherein said active surface element comprises a wire having a low thermal mass to allow for rapid heating and cooling.

13. The apparatus according to claim 12, wherein said wire comprises a filament.

14. The apparatus according to claim 12, wherein said wire comprises a ribbon.

15. The apparatus according to claim 12, wherein said wire is formed of a transition metal.

16. The apparatus according to claim 15, wherein said wire comprises one from among the following group of nichrome, nickel, platinum, rhodium, iridium, gold and silver.

17. The apparatus according to claim 12, wherein said wire is coiled to maximize said surface area of said active surface element.

18. The apparatus of claim 12, wherein said active surface element further comprises a sensor for monitoring and controlling the temperature of the active surface element.

19. The apparatus of claim 18, wherein said sensor comprises a thermocouple positioned along and connected to said wire.

20. The apparatus of claim 19, wherein said sensor further includes a monitoring circuit connected to the thermocouple for monitoring a rate of temperature change of said wire.

21. A method for increasing the sensitivity of an ion mobility spectrometer to trace chemical vapors in a gaseous sample, comprising the steps of:
   collecting amounts of said vapors from said sample of gas to be analyzed;
   desorbing said vapors within a reaction region of said ion mobility spectrometer;
   whereby the sensitivity of detection of said ion mobility spectrometer is increased by an enrichment factor which is the ratio of post-enrichment concentration to pre-enrichment concentrations of said vapors.

22. The method of claim 21, wherein said collecting step further comprises adsorbing and condensing said vapors on a cool surface area of an active surface element, and said desorbing step further comprises thermally releasing said vapors by heating said active surface element in the reaction region of said ion mobility spectrometer.

23. The apparatus according to claim 21, wherein said enrichment factor is greater than one.

24. The method according to claim 21, further comprising the step of controlling a temperature of the surface area of said active surface element during said collecting step.

25. A method for increasing the sensitivity of an ion mobility spectrometer to chemical compounds which are involatile, comprising the steps of:
   dissolving said chemical compounds in a solvent to form a solution;
   depositing said solution on said active surface element;
   evaporating said solvent, thereby leaving a residue of said involatile chemical compound on said active surface element;
   desorbing said residue from said active surface element within a reaction region of said ion mobility spectrometer.

26. The method according to claim 25, wherein said evaporating step further comprises controlling the temperature of said active surface element.

27. The method according to claim 25, wherein as sensitivity of detection of an ion mobility spectrometer is increased in accordance with an amount and a concentration of said solution deposited on said active surface element.

28. A method for increasing the sensitivity of an ion mobility spectrometer to solid particulates having a chemical species absorbed thereon, comprising the steps of:
   impinging said particulates on an active surface element to collect said particulates thereon;
   transferring said active surface element with said collected particulates into said reaction region of said ion mobility spectrometer;
   heating said active surface element to desorb said chemical species from said particulates within the reaction region of said ion mobility spectrometer.

29. The method according to claim 28, wherein said chemical species are absorbed to particles formed of one from among a group comprising ambient dust, finely ground alumina, glass, alumina-silicate, Tenax TM, or diatomaceous earth.

30. A method for increasing the sensitivity of a an ion mobility spectrometer to aerosol particulates, comprising the steps of:
   impinging said aerosol particulates on an active surface element to form condensation thereon;
   transferring said active surface element with condensation into said reaction region of said ion mobility spectrometer;
   heating said active surface element to desorb said condensation to form a vapor in the reaction region of said ion mobility spectrometer.

* * * * *

UNITED STATES PATENT AND TRADEMARK OFFICE
CERTIFICATE OF CORRECTION

PATENT NO. : 5,083,019
DATED : January 21, 1992
INVENTOR(S) : Spangler

It is certified that error appears in the above-identified patent and that said Letters Patent is hereby corrected as shown below:

In column 5, line 38, insert the following three lines:

-- E = enrichment factor --
-- $\tau$ = sticking probability --
-- P = pressure --

Signed and Sealed this

Twenty-fourth Day of August, 1993

Attest:

BRUCE LEHMAN

Attesting Officer

Commissioner of Patents and Trademarks